(12) United States Patent
Wildeman et al.

(10) Patent No.: US 8,632,517 B2
(45) Date of Patent: Jan. 21, 2014

(54) TWO BAR STITCH BONDED LOOP FASTENER FOR DIAPER AND RELATED METHOD

(75) Inventors: Martin Wildeman, Spartanburg, SC (US); Lori Shannon Sears, Taylors, SC (US)

(73) Assignee: Tietex International, Ltd, Spartanburg, SC (US)

( * ) Notice: Subject to any disclaimer, the term of this patent is extended or adjusted under 35 U.S.C. 154(b) by 513 days.

(21) Appl. No.: 12/804,409

(22) Filed: Jul. 21, 2010

(65) Prior Publication Data

US 2011/0028936 A1 Feb. 3, 2011

Related U.S. Application Data

(60) Provisional application No. 61/230,033, filed on Jul. 30, 2009.

(51) Int. Cl.
*A61F 13/15* (2006.01)
(52) U.S. Cl.
USPC ........... 604/391; 604/389; 604/387; 604/394; 604/396
(58) Field of Classification Search
USPC .......................... 604/391, 389, 387, 394, 396
See application file for complete search history.

(56) References Cited

U.S. PATENT DOCUMENTS

| 4,931,343 | A | 6/1990 | Becker et al. |
| 6,158,255 | A * | 12/2000 | Ternon ............................ 66/194 |
| 6,855,392 | B2 | 2/2005 | Wildeman et al. |
| 6,869,660 | B2 | 3/2005 | Wildeman |
| 7,294,387 | B2 | 11/2007 | Wildeman |
| 2004/0020579 | A1 * | 2/2004 | Durrance et al. ............... 156/66 |
| 2008/0280094 | A1 | 11/2008 | Wildeman et al. |

OTHER PUBLICATIONS

European Search Report for Corresponding Application No. EP 10007860.9 (six pages) issued Oct. 26, 2010.

* cited by examiner

*Primary Examiner* — Jacqueline F. Stephens
(74) *Attorney, Agent, or Firm* — J.M. Robertson, LLC

(57) ABSTRACT

A tear away diaper fastening system including a segment of loop material having a plurality of outwardly projecting loop elements adapted to engage cooperating hooking elements in juxtaposed contacting relation. The loop material includes a composite sheet of stitch bonded construction including a polymer film substrate layer. A first plurality of yarn elements extends in stitched relation through the substrate layer to define a plurality of parallel stitch lines of flat stitches extending along the machine direction of the sheet material to form a ground layer substantially covering an upper surface of the substrate layer. A second plurality of yarn elements extends in stitched relation through the substrate layer in zigzag crossing relation between parallel needle lines to define a plurality of raised loops extending above the ground layer.

17 Claims, 3 Drawing Sheets

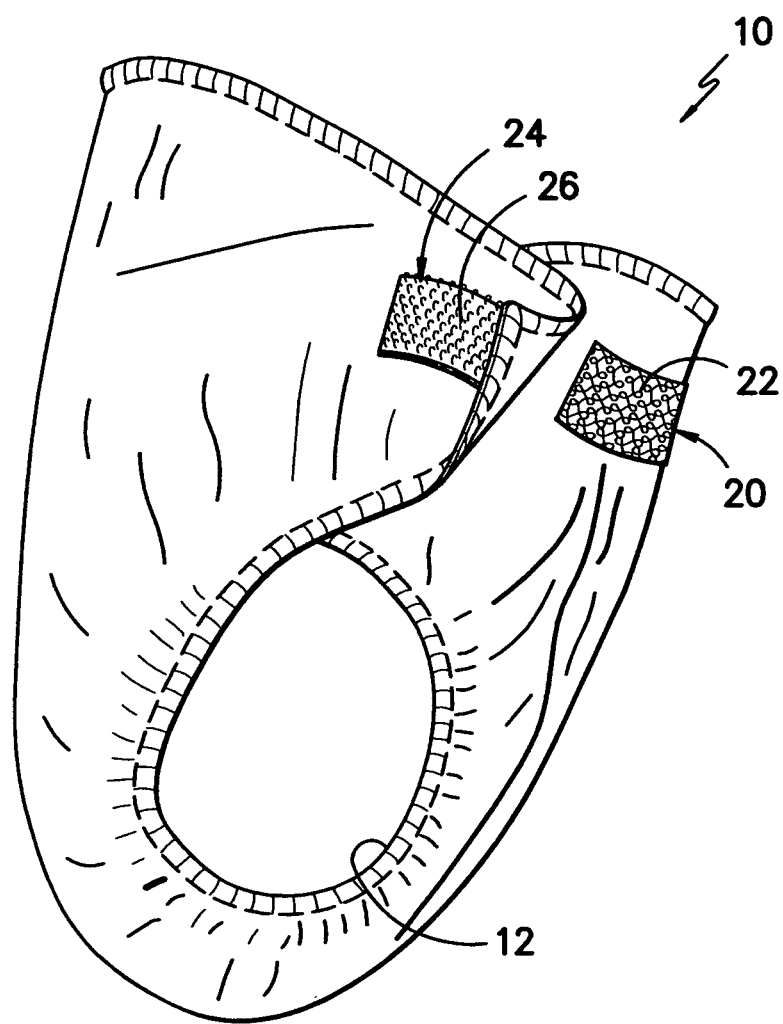
FIG. −1−

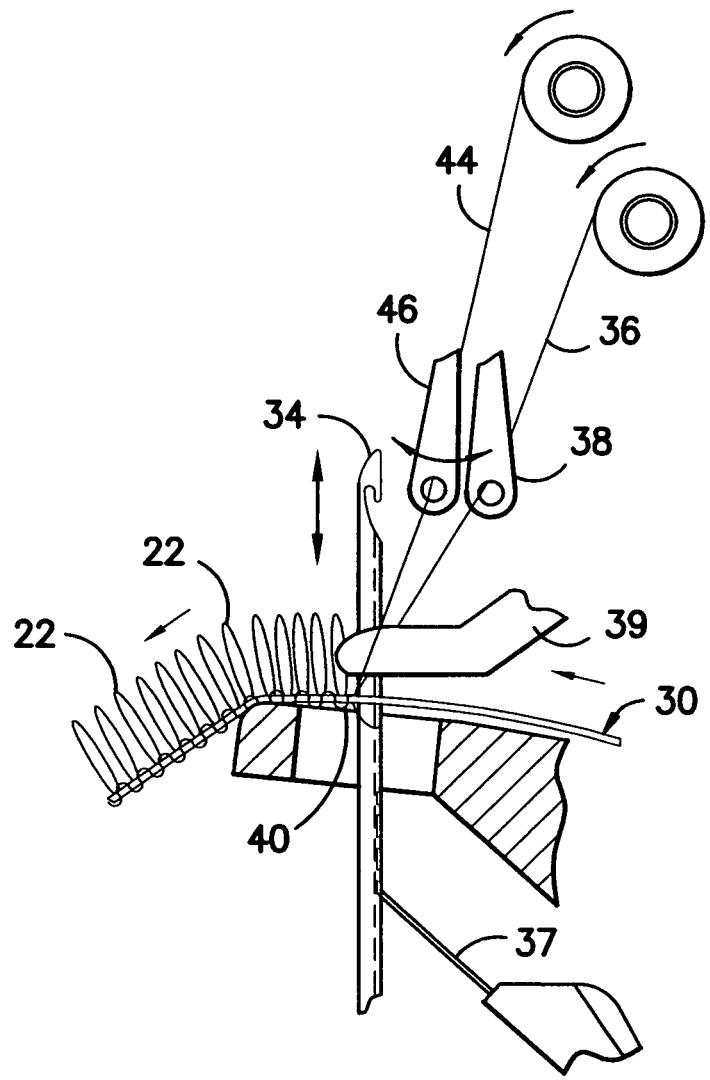
FIG. —2—

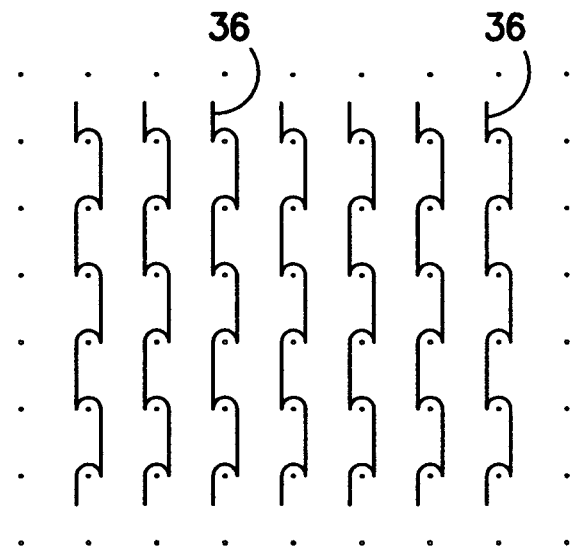
FIG. -3-
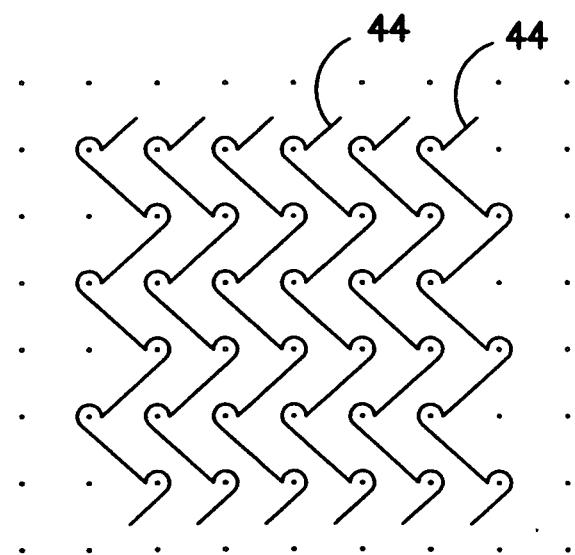
FIG. -4-

TWO BAR STITCH BONDED LOOP FASTENER FOR DIAPER AND RELATED METHOD

CROSS-REFERENCE TO RELATED APPLICATION

This non-provisional application claims the benefit of, and priority from, U.S. provisional application 61/230,033 filed Jul. 30, 2009 the contents of which are hereby incorporated by reference in their entirety as if fully set forth herein.

TECHNICAL FIELD

The present invention relates to a hook and loop fastening system, and more particularly, to a hook and loop fastening system incorporating a loop face composite material of stitch bonded construction including an arrangement of spaced surface loops disposed across at least one surface. The loop face composite material includes a first yarn system defining an arrangement of flat stitches stitched through a polymeric film or other light weight substrate to form a ground covering across the substrate and a second yarn system stitched through the substrate defining an arrangement of surface loops of yarn extending above the ground covering. The loop face composite material is adapted for use as the loop portion of a tear-away fastening system adapted to engage a cooperating hooking surface. The loop face material may find use as a landing zone for a fastening tab in a diaper or other environment of use.

BACKGROUND OF THE INVENTION

Tear away or contact fastening systems are well known. Such systems incorporate two opposing segments of material which are engageable in substantially juxtaposed relation to one another. A male portion of such a contact fastening system typically incorporates a plurality of outwardly projecting hooking structures, while the female portion incorporates a plurality of outwardly projecting loop structures. Upon engagement between the two cooperating portions, the hooking structures engage the opposing loop structures thereby establishing a bond. This bond may be broken by the application of a peeling action between the two opposing portions of material thereby permitting the male and female portions to be progressively disengaged from one another. The engagement may be reactivated by simply bringing the male and female portions back into contacting juxtaposed relation with one another.

In many environments, it is desirable for the connection between the hooking portion and the loop portion to remain secure during use. The strength of the bond formed by the hook and loop portions may be measured both in terms of peel strength and shear strength. In this regard, peel strength is the magnitude of the force required to pull the hook and loop portions away from one another by application of a pulling force having a direction oriented substantially normal to the plane defined by the interface between the joined materials. Accordingly, peel strength is generally reflective of the separating force experienced under normal use conditions. A standard technique for measurement of peel strength is set forth in ASTM standard 5170, the contents of which are incorporated herein by reference.

Shear strength is the magnitude of the force required to move the hook and loop portions away from one another by application of a pulling force having a direction oriented substantially parallel to the plane defined by the interface between the joined materials. A standard technique for measurement of shear strength is set forth in ASTM standard 5169, the contents of which are incorporated herein by reference.

Stitch-bonding is a known process in which yarns are stitched through a substrate to form a coordinated web structure. By way of example only, and not limitation, exemplary stitch-bonding processes are disclosed in U.S. Pat. Nos. 6,855,392; 6,869,660; and 7,294,387 all of which are incorporated by reference as if fully set forth herein. In the past, it has been difficult to achieve a combination of both high peel strength and high shear strength in a fastening system incorporating a loop fabric of stitch-bonded

SUMMARY OF THE INVENTION

The present invention provides advantages and alternatives over the prior art by providing a composite loop face fabric which incorporates a multi-bar stitch-bonded construction and related fastening system. A first yarn system forms an arrangement of flat stitches extending in stitched relation through a very light weight film or other substrate defining a ground covering across the substrate. A second yarn system forms an arrangement of loops above the ground covering. The combination of the stitching patterns for the first yarn system and the second yarn system provides remarkably high peel strength and shear strength levels.

In accordance with one exemplary aspect, the present invention provides a fastening system for a diaper. The fastening system includes a fastening tab including a segment of hook material having a plurality of outwardly projecting hooking elements. The fastening system further includes a segment of loop material disposed at a portion of the diaper remote from the fastening tab. The segment of loop material has outwardly projecting loop elements adapted to engage the hooking elements in juxtaposed contacting relation. The loop material includes a polymer film substrate layer having a mass per unit area of not greater than 100 grams per square meter. A first plurality of yarn elements extends in stitched relation through the substrate layer to define a plurality of parallel stitch lines of flat stitches extending along the machine direction of the sheet material. The parallel stitch lines of flat stitches cooperatively form a ground layer substantially covering an upper surface of the substrate layer. A second plurality of yarn elements extends in stitched relation through the substrate layer in zigzag crossing relation between parallel needle lines to define raised loops extending above the ground layer.

In accordance with another exemplary aspect, the present invention provides a method for forming a composite sheet material of stitch bonded construction adapted to be used as a loop portion of a tear away fastening system in a diaper. The method includes feeding a polymer film substrate layer of low density polyethylene to a stitch-forming position in a stitch bonding apparatus at an overfeed level of at least 0.1%. The polymer film substrate layer has a mass per unit area of not greater than 100 grams per square meter. Stitching a first plurality of yarn elements through the substrate layer to form a plurality of parallel stitch lines of flat stitches extending along the machine direction of the composite sheet material such that the parallel stitch lines of flat stitches cooperatively form a ground layer substantially covering an upper surface of the substrate layer. The flat stitches are present at a stitch notation of (1-0, 0-1). A second plurality of yarn elements are stitched through the substrate layer in zigzag crossing relation between parallel needle lines to define a plurality of raised loops extending above the ground layer. The second plurality of yarn elements is present at a stitch notation of (0-1, 2-1).

Other exemplary aspects of the invention will become apparent upon review of the following detailed description of preferred embodiments and practices.

BRIEF DESCRIPTION OF THE DRAWINGS

The accompanying drawings, which are incorporated in, and which constitute a part of this specification, illustrate exemplary constructions and procedures in accordance with the present invention and, together with the general description of the invention given above and the detailed description set forth below, serve to explain the principles of the invention wherein:

FIG. 1 illustrates a diaper incorporating a fastening arrangement utilizing cooperating hook and loop structures;

FIG. 2 illustrates schematically a two bar stitch-bonding process for selectively forming a surface loop yarn system and a cooperating ground yarn system through a substrate;

FIG. 3 is a needle point diagram illustrating a stitch forming arrangement for forming ground stitches across a substrate; and FIG. 4 is a needle point diagram illustrating a stitch forming arrangement for forming loop elements across a substrate.

While the invention has been illustrated and generally described above and will hereinafter be described in connection with certain potentially preferred embodiments and practices, it is to be understood that in no event is the invention limited to such illustrated and described embodiments and practices. On the contrary, it is intended that the present invention shall extend to all alternatives and modifications as may embrace the general principles of this invention within the full and true spirit and scope thereof.

DESCRIPTION OF THE PREFERRED EMBODIMENT(S)

Turning now to the drawings, in FIG. 1 there is illustrated a diaper 10 including a leg opening 12 and a releasable, adjustable fastening assembly. The fastening assembly incorporates a first segment of material 20 including a plurality of outwardly projecting loop elements 22 and a second segment of material 24 incorporating a plurality of outwardly projecting hooking elements 26. By the term "hooking elements" is meant elements having a geometry adapted to releaseably engage the loop elements 22 upon contact. By way of example only, and not limitation, such hooking elements 26 may be configured to have a hooked terminal end and/or an enlarged terminal end such as a "mushroom" shape or the like to become engaged within the loop elements 22. Of course it is to be appreciated that the relative position of the first segment of material 20 incorporating the loop elements 22 and the second segment of material 24 incorporating the hooking elements 26 may be reversed if desired. However, in a diaper, the material forming the loop elements 22 is most typically disposed across a zone overlying a user's abdominal region as shown and will define a landing zone for the hooking elements 22 which are typically disposed across outwardly extending tabs.

It is to be appreciated that the length of one or both of the first and second segments of material 20, 24 may be adjusted so as to provide a desired arrangement for properly adjusting the diaper 10. By way of example only and not limitation, it is contemplated that in the illustrated arrangement wherein the first segment of material 20 incorporating the loop elements 22 is disposed across a forward portion of the diaper 10, such first segment of material 20 may extend across an extended length thereby providing an extended landing zone surface for engagement with the second segment of material 24 during the joining process. This arrangement may facilitate adjustment of the diaper 10 to users of various size.

The first segment of material 20 is of a so called "stitch bonded" construction having substantially parallel rows of stitches extending through a substrate. Such materials may be formed using a multi-bar stitch bonding apparatus as illustrated schematically in FIG. 2 and the operation of which will be well known to those of skill in the art.

In the illustrated practice, a light weight substrate material 30 is conveyed to a stitch-forming position in the direction indicated by the arrow. By way of example only, and not limitation, one potentially desirable substrate material is a low-density polymeric film such as low density polyethylene (LDPE) or the like. In accordance with one exemplary practice, the substrate material may be a polymeric film having a mass per unit area of not more than 100 grams per square meter. In accordance with another exemplary practice, the substrate material may be a polymeric film having a mass per unit area of about 5 to 50 grams per square meter. One such exemplary film is a 1-mil thickness LDPE film having a mass per unit area of about 23 grams per square meter sold under the trade designation FT-540 by Filmtech, Inc. having a place of business at Allentown, Pa. However, other materials and/or different weights and thicknesses may likewise be used if desired. According to one potentially preferred practice, the substrate material 30 is slightly overfed to the stitch-forming position to provide a surplus of substrate material thereby reducing or eliminating internal tension in the substrate during stitching. In this regard, an overfeed rate of about 0.1% or greater may be desirable. An overfeed rate of about 0.1% to about 50% may be preferred and an overfeed rate of about 0.1% to about 5% may be particularly preferred during formation of loop elements 22.

As will be appreciated by those of skill in the art, the stitch-forming position is defined by a row of reciprocating needles 34, extending in adjacent relation to one another across the width of the substrate material 30 substantially transverse to the direction of movement of the substrate material 30. While only a single needle has been illustrated, in actual practice a large number of such needles are arranged in close relation to one another in the cross-machine direction between the fingers 39 of a sinker bar. It is contemplated that the so-called gauge or needle density in the cross machine direction may be adjusted as desired. By way of example only, and not limitation, it is contemplated that the needle density may be in the range of about 7 to about 28 needles per inch and more preferably about 12 to about 16 needles per inch and most preferably about 14 needles per inch, although higher and lower needle densities may likewise be used if desired. In accordance with one embodiment, the stitch density in the machine direction may be in the range of about 5 to 20 courses per inch, and more preferably about 8 to 12 courses per inch, although higher and lower machine direction stitch densities may likewise be used if desired.

According to the illustrated practice, two yarns systems (i.e. two bars) are used to form stitches through the substrate material 30. In the illustrated two bar practice, ground yarns 36 forming a first yarn system are carried through a first set of moveable yarn guides 38 manipulated by a back guide bar (not shown) for engagement with needles 34, across the width of the substrate material 30. While only a single ground yarn 36 is illustrated, it will be understood that in practice multiple ground yarns are present across the width of the stitch-forming apparatus. By way of example only, and not limitation, the ground yarns 36 may have a linear density of about 20 denier to about 300 denier. One such suitable yarn for use in a diaper attachment is 40-denier/12 filament fully oriented polyester yarn. However, other yarn constructions and filament counts including monofilament may likewise be utilized if desired.

According to the potentially preferred practice, the ground yarns 36 are in a fully threaded arrangement to engage each needle. In operation, each ground yarn 36 preferably engages a single needle 34 which moves up and down in a reciprocating manner through the substrate material 30. As will be appreciated by those of skill in the art, in operation, the needle 34 engages a closing wire 37 to close the needle on the downstroke and to reopen it on the upstroke so as to form an arrangement of stitch lines running in the machine direction along the length of the substrate material. As illustrated schematically in FIG. 2, the ground yarns 36 do not cross between needle lines and thus do not pass over the fingers 39 of the sinker bar. According to one desirable practice, the stitch lines formed by the ground yarns 36 are sufficiently close to cover the upper surface of the substrate material 30.

The loop elements 22 may be formed by a loop yarn 44 threaded through moveable yarn guides 46 carried by a front guide bar (not shown). The loop yarn 44 is preferably substantially fully threaded relative to the needles 34. While only a single loop yarn 44 is illustrated for explanatory purposes, it is to be understood that in actual practice, multiple loop yarns 44 are used across the width of the fabric. By way of example only, and not limitation, the loop yarns 44 may have a linear density of about 20 denier to about 300 denier. One such suitable yarn for use in a diaper attachment is a 40 denier/12 filament fully oriented polyester yarn. However, other yarn constructions and filament counts including monofilament may likewise be utilized if desired.

In the fully threaded arrangement, the loop yarns 44 will form a substantially continuous pattern of loop elements 22. The loop elements 22 are formed by passing the loop yarns 44 back and forth in a zigzag pattern between adjacent needles 34 over the fingers 39 of the sinker bar. During the stitch-forming reciprocating action of the needles 34, the fingers 39 of the sinker bar hold the crossing segments of the loop yarns above the substrate, thereby yielding upstanding loops rather than flat stitches. By way of example only, a pile sinker height of about 2 mm may be used. However, other heights may be used if desired.

It has been found that the combination of stitch patterns selected for the ground yarns 36 and the loop yarns 44 has a surprising influence on the peel strength and the shear strength in a final hook and loop fastening system. In particular, it has been found that a stitching arrangement in which the ground yarn is stitched in a pattern (1-0, 0-1) as illustrated schematically in FIG. 3 and the loop yarn is stitched in a pattern (0-1, 2-1) as illustrated schematically in FIG. 4, yields a peel strength which is significantly higher than other similar stitch pattern combinations using identical yarns.

WORKING EXAMPLE

A loop fabric was produced on a two-bar stitch-bonding machine set at a gauge of 14 needles per inch in the cross-machine direction and set to stitch 9.2 courses per inch in the machine direction. Both the front bar and the back bar were fully threaded with 40 denier, 12 filament draw warped polyester yarn. The substrate was a 1-mil thickness LDPE film having a mass per unit area of 23 grams per square meter delivered at 0.5% overfeed. For the back bar carrying the ground yarn, the so called "runner length" defined as the yarn length consumed per 480 stitch rack was 4050 inches. For the front bar carrying the loop yarn, the runner length was 5500 inches. The back bar stitch notation for the ground yarn stitches was set at (1-0,0-1) as illustrated schematically in FIG. 3. The front bar stitch notation for the loop yarn stitches was set at (0-1,2-1) as illustrated schematically in FIG. 4. The pile sinker height for the loop yarn was 2 millimeters.

The formed loop fabric was used to engage a standard hook fabric 20 mm hook tape by 3M. Following engagement between the hook fabric and the loop fabric, both peel strength and shear strength were measured. The results are set forth below with values rounded to the nearest whole number.

| | |
|---|---|
| Mean Peel Strength (grams force per inch) | 252 |
| Mean Shear Strength (grams force per square inch) | 10,620 |

COMPARATIVE EXAMPLES

Stitch-bonded loop fabric constructions were formed using various combinations of stitch notations for the front bar (FB) and the back bar (BB). Peel strength and shear strength were then measured using the same hook fabric as used in the working example above. The construction details and measured strength characteristics are set forth in the table below

| FB yarn | BB Yarn | FB Stitch | BB Stitch | FB Runner | BB Runner | CPI | Mean Peel gm/in | Mean Shear GM/SI |
|---|---|---|---|---|---|---|---|---|
| 40/12 | 40/12 | 1-0, 1-2 | 1-0, 1-0 | 5500 | 4050 | 9.2 | 80 | 6287 |
| 40/12 | 40/12 | 1-0, 1-2 | 1-0, 1-0 | 4600 | 3000 | 12 | 101 | 7611 |
| 40/12 | 40/12 | 1-0, 1-2 | 1-0, 1-0 | 3600 | 2500 | 14 | 133 | 7053 |
| 40/12 | 40/12 | 1-0, 2-3 | 1-0, 1-0 | 5070 | 4050 | 9.2 | 154 | 7689 |
| 40/12 | 40/12 | 1-0, 2-3 | 1-0. 1-0 | 4950 | 3350 | 12 | 175 | 7830 |
| 40/12 | 70/34 | 1-0, 1-1, 1-2, 1-1 | 1-0, 1-0 | 3600 | 4000 | 9.2 | 116 | 7519 |
| 40/12 | 70/34 | 1-0, 1-1, 1-2, 1-1 | 1-0, 1-0 | 1800 | 3225 | 12 | 73 | 8770 |
| 40/12 | 70/34 | 1-0, 2-1 | 1-0, 1-0 | 5400 | 4100 | 9.2 | 141 | 9674 |
| 40/12 | 70/34 | 1-0, 2-1 | 1-0, 1-0 | 4150 | 3250 | 12 | 134 | 8712 |
| 40/12 | 70/34 | 1-0, 2-1, 1-0, 1-2 | 1-0, 1-0 | 5050 | 4075 | 9.2 | 168 | 10895 |
| 40/12 | 70/34 | 1-0, 2-1, 1-0, 1-2 | 1-0, 1-0 | 4150 | 3250 | 12 | 159 | 9361 |

As can be seen, the highest mean peel strength achieved was approximately 175 grams force per inch. However, this construction yielded a relatively modest mean shear strength of only about 7,830 grams force per square inch. The best overall combination of the comparative study provided a mean peel strength of approximately 168 grams force per inch with a mean shear strength of about 10,895 grams force per square inch. However, even the highest peel strength achieved in the comparison trials was only about 70% of the level achieved in the inventive working example.

It is to be understood that while the present invention has been illustrated and described in relation to certain potentially preferred embodiments, constructions and procedures, that such embodiments, constructions and procedures are illustrative only and that the present invention is in no event to be limited thereto. Rather, it is contemplated that modifications and variations embodying the principles of this invention will no doubt occur to those of skill in the art. It is therefore contemplated and intended that the present invention shall extend to all such modifications and variations as may incorporate the broad aspects of the invention within the full spirit and scope thereof.

The invention claimed is:

1. A fastening system for a diaper, the fastening system comprising: a fastening tab including a segment of hook material having a plurality of outwardly projecting hooking elements; and
   a segment of loop material disposed at a portion of the diaper remote from the fastening tab, the segment of loop material including a plurality of outwardly projecting loop elements adapted to engage the hooking elements in juxtaposed contacting relation, wherein the loop material comprises a composite sheet of stitch bonded construction including a polymer film substrate layer having a mass per unit area of not greater than 100 grams per square meter, the composite sheet of stitch bonded construction further including a first plurality of yarn elements extending in stitched relation through the substrate layer to define a plurality of parallel stitch lines of flat stitches extending along the machine direction of the sheet material, wherein the parallel stitch lines of flat stitches cooperatively form a ground layer substantially covering an upper surface of the substrate layer, and wherein the composite sheet of stitch bonded construction further includes a second plurality of yarn elements extending in stitched relation through the substrate layer in zigzag crossing relation between parallel needle lines to define said plurality of outwardly projecting loop elements extending above the ground layer and wherein the second plurality of yarn elements is present at a stitch notation of (0-1, 2-1).

2. The fastening system for a diaper as recited in claim 1, wherein the flat stitches are present at a stitch notation of (1-0, 0-1), and wherein the second plurality of yarn elements is present at a stitch notation of (0-1, 2-1).

3. The fastening system for a diaper as recited in claim 1, wherein the polymer film substrate layer is low density polyethylene.

4. The fastening system for a diaper as recited in claim 3, wherein the polymer film substrate layer has a mass per unit area of about 5 to 50 grams per square meter.

5. The fastening system for a diaper as recited in claim 3, wherein the polymer film substrate layer has a mass per unit area of about 20 to 30 grams per square meter.

6. The fastening system for a diaper as recited in claim 3, wherein the polymer film substrate layer is present at an overfeed level of about 0.1% to 50%.

7. The fastening system for a diaper as recited in claim 3, wherein the polymer film substrate layer is present at an overfeed level of about 0.1% to 5%.

8. The fastening system for a diaper as recited in claim 1, wherein the first plurality of yarn elements are multi-filament polyester yarns having a linear density of about 20 to 60 denier.

9. The fastening system for a diaper as recited in claim 1, wherein the second plurality of yarn elements are multi-filament polyester yarns having a linear density of about 20 to 60 denier.

10. The fastening system for a diaper as recited in claim 1, wherein the first plurality of yarn elements are multi-filament polyester yarns having a linear density of about 20 to 60 denier, and wherein the second plurality of yarn elements are multi-filament polyester yarns having a linear density of about 20 to 60 denier.

11. The fastening system for a diaper as recited in claim 1, wherein the segment of loop material is disposed at a position on the diaper overlying a user's abdominal region.

12. A fastening system for a diaper, the fastening system comprising: a fastening tab Including a segment of hook material having a plurality of outwardly projecting hooking elements; and
    a segment of loop material disposed at a portion of the diaper remote from the fastening tab at a position on the diaper overlying a user's abdominal region, the segment of loop material including a plurality of outwardly projecting loop elements adapted to engage the hooking elements in juxtaposed contacting relation, wherein the loop material comprises a composite sheet of stitch bonded construction including a polymer film substrate layer of low density polyethylene present in an overfed condition, wherein the polymer film substrate layer has a mass per unit area of about 5 to 50 grams per square meter, the composite sheet of stitch bonded construction further including a first plurality of yarn elements extending in fully threaded stitched relation through the substrate layer to define a plurality of parallel stitch lines of flat stitches extending along the machine direction of the sheet material without crossing between needle lines, wherein the parallel stitch lines of flat stitches cooperatively form a ground layer substantially covering an upper surface of the substrate layer, and wherein the flat stitches are present at a stitch notation of (1-0, 0-1), and wherein the composite sheet of stitch bonded construction further includes a second plurality of yarn elements extending in fully threaded stitched relation through the substrate layer in zigzag crossing relation between parallel needle lines to define said plurality of outwardly projecting loop elements extending above the ground layer, the second plurality of yarn elements being present at a stitch notation of (0-1, 2-1).

13. The fastening system for a diaper as recited in claim 12, wherein the polymer film substrate layer has a mass per unit area of about 20 to 30 grams per square meter.

14. The fastening system for a diaper as recited in claim 12, wherein the polymer film substrate layer is present at an overfeed level of about 0.1% to 5%.

15. The fastening system for a diaper as recited in claim 12, wherein the first plurality of yarn elements are multi-filament polyester yarns having a linear density of about 20 to 60 denier.

16. The fastening system for a diaper as recited in claim 12, wherein the second plurality of yarn elements are multi-filament polyester yarns having a linear density of about 20 to 60 denier.

17. The fastening system for a diaper as recited in claim 12, wherein the first plurality of yarn elements are multi-filament polyester yarns having a linear density of about 20 to 50 denier, and wherein the second plurality of yarn elements are multi-filament polyester yarns having a linear density of about 20 to 60 denier.

* * * * *